US006743934B2

(12) United States Patent
Saito et al.

(10) Patent No.: US 6,743,934 B2
(45) Date of Patent: Jun. 1, 2004

(54) RAW MATERIAL COMPOUNDS FOR USE IN CVD, AND CHEMICAL VAPOR DEPOSITION OF RUTHENIUM COMPOUND THIN FILMS

(75) Inventors: Masayuki Saito, Hiratsuka (JP); Takeyuki Sagae, Hiratsuka (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 10/417,197

(22) Filed: Apr. 17, 2003

(65) Prior Publication Data

US 2003/0203102 A1 Oct. 30, 2003

(30) Foreign Application Priority Data

Apr. 18, 2002 (JP) ...................... P2002-116054

(51) Int. Cl.[7] ........................ C07F 15/00; C23C 16/18
(52) U.S. Cl. ................ 556/40; 556/136; 556/137; 427/124; 427/126.5; 427/227; 427/585; 427/593; 106/287.18; 106/287.24
(58) Field of Search .................. 556/40, 136; 555/137; 427/124, 126.5, 227, 585, 593; 106/287.18, 287.24

(56) References Cited

U.S. PATENT DOCUMENTS 3,804,868 A * 4/1974 Chabardes et al. ........... 556/21

FOREIGN PATENT DOCUMENTS

JP   2000-212744   8/2000

* cited by examiner

*Primary Examiner*—Porfirio Nazario-Gonzalez
(74) *Attorney, Agent, or Firm*—Rothwell, Figg, Ernst & Manbeck, P.C.

(57) ABSTRACT

This invention provides raw material compounds for use in CVD which contain organic ruthenium compounds as a main ingredient, the organic ruthenium compounds having two β-diketones plus one diene, one diamine or two organic ligands which are coordinated with ruthenium. In this invention, the vapor pressures of the organic ruthenium compounds are made preferable by specifying the number of the carbon atoms contained in the above β-diketones and the types of the above diene etc.

10 Claims, No Drawings

RAW MATERIAL COMPOUNDS FOR USE IN CVD, AND CHEMICAL VAPOR DEPOSITION OF RUTHENIUM COMPOUND THIN FILMS

BACKGROUND OF THE INVENTION

1. Field of the Invention

This invention relates to raw materials for producing ruthenium or ruthenium compound thin films by CVD.

2. Description of the Related Art

In recent years, ruthenium or ruthenium compounds have been being applied as materials for thin film electrodes used in semiconductor devices such as DRAM and FERAM. This is because these materials are extremely excellent in electric properties such as specific resistance, and, for example in DRAM, the use of the materials for the storage electrodes of its capacitors have been examined and is considered to be able to contribute largely to higher density DRAM. And ruthenium or ruthenium compound thin films have been expected to become one of the key materials for thin film electrodes and attracted considerable attention.

As the method for producing ruthenium or ruthenium compound thin films, not only sputtering, but also chemical vapor deposition (hereinafter referred to as CVD) is often used. The reason that CVD is often used is that it makes it easier to produce uniform thin films, in addition, it is superior to sputtering in step coverage.

Ruthenium compounds which have been expected to be materials for use in production of ruthenium or ruthenium compound thin films by CVD and the use of which has been examined include, for example, bis(ethylcyclopentadienyl)ruthenium having the formula shown below. This organic ruthenium compound is obtained by replacing hydrogen atoms of the two cyclopentadiene rings bis(cyclopentadienyl)ruthenium by ethyl groups.

[Chemical Formula 1]

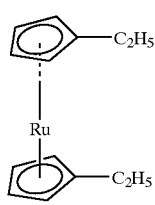

The compound, bis(ethylcyclopentadienyl)ruthenium, has been considered to be qualified as a CVD raw material because it is excellent in handling properties, due to its low melting point and the liquid state at room temperature, and in production efficiency, due to its high vapor pressure.

Further, in recent years, from the viewpoint of reduction of thin film production costs and effective use of resources, introduction of recycling techniques has also been examined for CVD raw materials. In such recycling, it is required to efficiently separate/purify unreacted compounds from used materials. In bis(ethylcyclopentadienyl)ruthenium, the unreacted compound is relatively easy to separate and refine, due to its high vapor pressure and good thermal stability, and its effective recycle is made possible by proper means such as distillation.

In thin film electrodes, it goes without saying that their purity and morphology are important, but on the other hand their adhesion to a substrate is also important. As a substrate for semiconductor devices, $SiO_2$ or a $SiO_2$ film is often used, a ruthenium thin film produced from bis(ethylcyclopentadienyl)ruthenium, however, has a problem of relatively low adhesion to $SiO_2$. And to cope with this problem, a method has been employed in which a Ru front-end is formed by sputtering before forming a thin film by CVD. However, this leads to increase in the number of processes. Thus, there have been demands for development of organic compounds which, as CVD raw materials, permit the production of thin films having higher adhesion properties.

To meet the demand for higher adhesion properties, organic ruthenium compounds having been proposed in recent years are tris(β-diketonato)ruthenium having the following formula (for further details of this compound, refer to Japanese Patent Laid-Open No. 2000-212744).

[Chemical Formula 2]

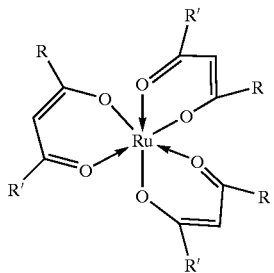

wherein R and R' represent different alkyl groups with 1 to 4 carbon atoms, respectively.

The above organic ruthenium compounds consist of ruthenium and three β-diketons coordinated therewith, and their states at room temperature differ depending on their substituents, in other words, there are tris(β-diketonato)ruthenium in the liquid state and those in the solid states. Since the compounds being in the solid state at room temperature are highly soluble in organic solvents, as long as they are dissolved in an organic solvent, they can be used as CVD raw materials. Thus, both liquid and solid tris(β-diketonato)ruthenium are said to be possibly used as CVD materials. Since the ruthenium thin films produced from tris(β-diketonato)ruthenium excel in adhesion to $SiO_2$, much hope is placed on these compounds, in this respect.

However, according to the inventors of this invention, in tris(β-diketonato)ruthenium which are in the liquid state at room temperature (such as tris(2,4-octadionato)ruthenium wherein $R_1$ is a methyl group and $R_2$ is a butyl group and tris(6-methyl-2,4-heptadionato)ruthenium wherein $R_1$ is a methyl group and $R_2$ is an isobutyl group), their thin film production efficiency is low because of their low vapor pressure, and to ensure a certain efficiency, the heating temperature must be increased at the time of thin film production. At the time of heating, if the vaporization temperature is increased higher than necessary and the raw materials are excessively heated, the compounds tend to decompose even in an inert atmosphere. Therefore, when producing their thin films using a large volume of raw material gas, it is difficult to control the heating of the raw materials. Thus, liquid β-diketonatoruthenium are unfit for thin film production on large-size substrate and mass production.

Further, if the vapor pressure is low, it is difficult to separate/purify the unreacted compounds from the used raw materials by distillation etc.; and moreover, in the above easy-to-decompose compounds, the amount of the unreacted compounds remaining in the used raw materials is very small, and even if they can be separated, it is impossible to recover them efficiently. Thus the use of these compounds for forming thin films results in higher production costs.

As to the solid tris(β-diketonato)ruthenium, taking into consideration their recycling, they are not necessarily preferable, even if they can be used as CVD raw materials once they are dissolved in solvents. The reason is that it is often difficult to recover solid matters by distillation once they are dissolved in liquids.

Thus, though tris(β-diketonato)ruthenium have the advantage of providing thin films with good adhesion, they still have problems of being low in thin film production efficiency due to their low vapor pressure and in possibility of their recycling.

This invention has been made in light of the above described background. Accordingly, an object of this invention is to provide, on the assumption that the raw material compounds for use in production of ruthenium thin films or ruthenium compound thin films by CVD are in the liquid state at room temperature, organic ruthenium compounds which have the advantages the above described compounds have, that is, the advantages of having good thermal stability and high vapor pressure, and hence being fit for recycling and of being able to provide thin films with high adhesion to a substrate. Another object of this invention is to provide a method for producing thin films using the above organic ruthenium compounds.

SUMMARY OF THE INVENTION

To solve the above described problems, the inventors started with the analysis of the course of the formation of thin films in CVD and presumed the constitution of preferable compounds. In CVD, vaporized raw material compounds are carried on a substrate, and decomposed and oxidized on the same so that the object materials as constituents of thin films are deposited as thin films.

In the above described CVD, the process of ruthenium thin film formation consists mainly of two steps. The first step is a step of forming ruthenium crystal nucleuses on a substrate, which is also referred to as latent period or incubation period. In this step, there exists no thin film, but countless crystal nucleuses are dotted on the substrate and grow in the planar direction.

The substantial growth of ruthenium crystal as a thin film occurs in the step next to the first step (the latent period). In the step, the decomposition reaction of the raw material gas is accelerated by the catalytic action of the crystal nucleuses produced in the first step and thereby the rapid growth of the thin film is caused.

The inventors considered that the adhesion of thin films to a substrate depends largely on the number of crystal nucleuses produced in the first step and the thin films' affinity for the materials which consist of the substrate. In other words, the inventors considered that to produce thin films having good adhesion to a substrate, it is desirable to use, as raw materials, compounds capable of producing more crystal nucleuses having affinity for the substrate materials.

Then, the inventors examined tris(β-diketonato) ruthenium for the factors that permitted thin films of good adhesion to be formed. As a result, they found that Ru—O bonds contained in the molecule largely contributed to the adhesion of thin films to a substrate. According to the inventors, due to the Ru—O bonds, the crystal nucleuses produced on the substrate in the first step are deposited in the form similar to ruthenium oxide whose oxygen content is high, and the high adhesion properties of the crystal nucleuses similar to ruthenium oxide serve to improve the adhesion properties of thin films.

Based on the above mentioned consideration, the inventors concluded that to ensure the adhesion properties of thin films, organic compounds containing oxygen in their molecules are preferably used.

On the other hand, consideration of vapor pressure, which is the other problem to be solved by this invention, revealed that vapor pressure tended to be low in compounds having high molecular weights. And it is considered that, since many of the conventional tris(β-diketonato)ruthenium have three ligands (β-diketones), which have much higher molecular weights compared with the ligands of bis (ethylcyclopentadienyl)ruthenium, coordinated with ruthenium, the molecular weights of the ruthenium compounds become higher, which causes low vapor pressure.

Thus, based on the above mentioned consideration, the inventors concluded that preferable organic ruthenium compounds had β-diketones, which are ligands containing oxygen, coordinated with ruthenium and had low molecular weights. And compounds were examined which met the above requirement and the preconditions that they were in the liquid state at room temperature. As a result, they found the following three types of organic ruthenium compounds which have two β-diketones and specified ligands coordinated with ruthenium, and they finally thought of this invention.

A first type of organic metal compounds of this invention are raw material compounds for use in CVD which contain organic ruthenium compounds as a main ingredient, the organic ruthenium compounds having two β-diketones and one diene coordinated with ruthenium as shown by the following structural formula.

[Chemical Formula 3]

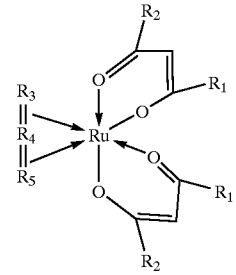

A second type of organic metal compounds of this invention are raw material compounds for use in CVD which contain organic ruthenium compounds as a main ingredient, the organic ruthenium compounds having two β-diketones and one diamine coordinated with ruthenium as shown by the following structural formula.

[Chemical Formula 4]

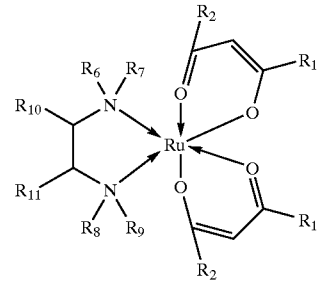

A third type of organic metal compounds of this invention are raw material compounds for use in CVD which contain organic ruthenium compounds as a main ingredient, the organic ruthenium compounds having two β-diketones and two organic ligands coordinated with ruthenium as shown by the following structural formula.

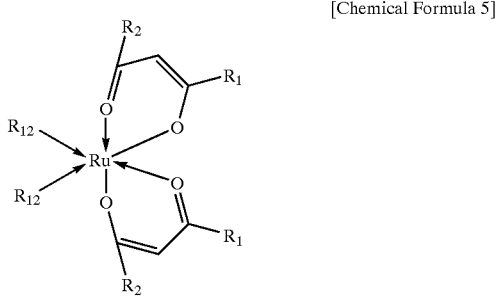

[Chemical Formula 5]

As described above, the three types of organic ruthenium compounds of this invention have a common characteristic of having two diketones, as a factor that improves the adhesion of their thin films, coordinated therewith, and they further have specified ligands, as a factor that ensures high vapor pressure and handling properties (possibility of keeping themselves in the liquid state) required for CVD raw materials, coordinated therewith.

The vapor pressures of the organic ruthenium compounds of this invention tend to be low as the molecular weights of the β-diketones coordinated with ruthenium of the organic ruthenium compounds of this invention become high, as aforementioned; therefore, in any of the organic ruthenium compounds of this invention, the β-diketones preferably have low molecular weights. Thus, in this invention, the substituents $R_1$, $R_2$ of the β-diketones are alkyl groups, respectively, and the total number of their carbon atoms is restricted within a prescribed range. Specifically, in the first type of ruthenium compounds, the total number of the carbon atoms of $R_1$ and $R_2$ is 3 to 5. The reason for this is that if the number of the carbon atoms is less than 3, the compounds are hard to keep in the liquid state at room temperature, whereas if the number of the carbon atoms is more than 5, the molecular weights of the ruthenium compounds become high and their vapor pressures become low. And for the same reason, in the second and third types of ruthenium compounds, the total number of the carbon atoms of $R_1$ and $R_2$ is 2 to 5.

Preferably, the substituents $R_1$ and $R_2$ of the β-diketones are different alkyl groups, in other words, the β-diketones are of asymmetrical shape. This is because the compounds which have the β-diketones of asymmetrical shape coordinated with ruthenium are easier to keep in the liquid state.

Taking into account the above conditions, the concrete examples of the β-diketones preferably used in this invention include, for example, 2,4-hexanedione, 5-methyl-2,4-hexanedione, 2,4-heptanedione, 5-methyl-2,4-heptanedione, 6-methyl-2,4-heptanedione and 2,4-octanedione. Of these β-diketones, preferably those having branched structure are selected for the ruthenium compounds, compared with those having straight-chain structure, because the ruthenium compounds having the β-diketones of branched structure coordinated therewith have higher vapor pressures. Accordingly, of the above examples, 5-methyl-2,4-hexanedione, 5-methyl-2,4-heptanedione and 6-methyl-2,4-heptanedione are particularly preferable.

At the same time, the organic ruthenium compounds of this invention have one diene or diamine coordinated with ruthenium. Selecting these ligands permits the organic ruthenium compounds of this invention to have high vapor pressures, and using such ruthenium compounds as CVD raw materials enables efficient thin film production.

The dienes coordinated with ruthenium of the first type of organic compounds are not limited to chain dienes, but may be cyclic dienes. Although the dienes have two double bonds per molecule, the relationship between the distance from one double bond to the other and the distance of d orbital of ruthenium affects the thermal stability of the compounds. According to the inventors, if the distance from one double bond to the other is too short, the coordination of the diene does not occur, whereas if the distance is too long, the thermal stability of the compounds is lowered even if the coordination occur. Preferably the molecular weights of the coordinated dienes are relatively low. Just like the case of β-diketones, the dienes having low molecular weights permit ruthenium compounds to have high vapor pressures. Taking into account these conditions, preferable coordinated dienes include, for example, 1,5-cyclooctadinene, norbornadiene and 1,4-cyclohexadiene.

Then, as to the diamines which are ligands of the second type of organic compounds, one of the requirement for the ligands is that they have low molecular weights. And, similar to the first type of compounds, the thermal stability of the second type of organic compounds depends on the relationship between the atomic distance between the two nitrogen atoms and the distance of d orbital of ruthenium. Taking this into account, the substituents $R_6$ to $R_8$ of the diamines are selected from hydrogen and alkyl groups and the total number of the carbon atoms is 2 to 8. And preferable coordinated diamines in this second type of compounds include, for example, N,N,N',N'-tetramethylethylenediamine.

In this patent application, are disclosed, as the third type of compounds, the organic ruthenium compounds which have two organic ligands coordinated with ruthenium. The requirements for the organic ligands are that they are what are called monodentates, they have low molecular weight, and that their bond strength to ruthenium is high. In particular, preferable organic ligands include, for example, olefins, amines, nitrites and carbonyls. As concrete examples of each organic ligand, the olefins include, for example, ethylene, propylene, 2-methylpropylene, butene, 2,4-butadiene. The amines include, for example, trimethylamine and triethylamine. And the nitrites include, for example, acetonitrile and acrylonitrile.

Then, the methods for producing the organic ruthenium compounds of this invention will be described. The organic ruthenium compounds of this invention consist of ruthenium and two types of organic ligands coordinated therewith, and there are two methods for producing the same.

A first production method includes the steps of: reacting a ruthenium compound with a diene compound, diamine compound or the like to produce a ruthenium diene compound etc. as a precursor; and reacting the precursor with a β-diketone compound to produce an object compound. This method is suitable for producing the first type of compounds (the compounds having a diene coordinated with ruthenium) of this invention. For example, in the method for producing bis(5-methyl-2,4-hexanedionato)(norbornadiene)ruthenium ($R_1$=methyl group, $R_2$=propyl group), which is one of the first type of organic ruthenium compounds of this invention, first a ruthenium compound (ruthenium chloride etc.) is reacted with norbornadiene in an organic solvent to produce norbornadieneruthenium chloride as a precursor. Then the norbornadieneruthenium chloride is reacted with 5-methyl- 2,4-hexanedione to produce bis(5-methyl-2,4-hexanedionato)(norbornadiene)ruthenium.

A second method includes the steps of: reacting a ruthenium compound with a β-diketone compound to produce tris(β-diketonato)ruthenium as a precursor; and reacting the precursor with a diene compound, diamine compound or the like to produce an object compound. This method is suitable for producing the second type of compounds (the compounds having a diamine coordinated with ruthenium) and the third type of compounds (the compounds having two organic ligands coordinated with ruthenium) of this invention. For example, in the method for producing bis(5-methyl-2,4-hexanedionato)(N,N,N',N'-tetramethylethylenediamine)ruthenium ($R_1$=methyl group, $R_2$=propyl group, $R_6$ to $R_{11}$=methyl groups), which is one of the second type of organic ruthenium compounds of this invention, first a ruthenium compound (ruthenium chloride etc.) is reacted with 5-methyl-2,4-hexanedione in water to produce tris(5-methyl-2,4-hexanedionato)ruthenium as a precursor. Then the precursor is reacted with N,N,N',N'-tetramethylethylenediamine to produce bis(5-methyl-2,4-hexanedionato)(N,N,N',N'-tetramethylethylenediamine) ruthenium.

Lastly, a method for forming thin films which applying CVD raw materials containing the organic ruthenium compounds of this invention as a main ingredient. The method is basically the same as the general type of CVD. Specifically, the method includes the steps of: vaporizing a raw material compound; carrying the vaporized raw material compound on a substrate; and decomposing the raw material to deposit ruthenium or a ruthenium compound on the substrate.

As to the vaporization of the raw material compounds, since the organic ruthenium compounds of this invention can be in the liquid state at room temperature, it may be performed by directly heating the organic ruthenium compounds or by dissolving the organic ruthenium compounds of this invention in proper solvents and heating the solution for vaporization. In the latter case, as a solvent are used organic solvents such as methanol, ethanol and propanol.

As to the system of vaporizing the raw materials, there are two types: one in which the raw materials stored in a raw material container is bubbled while heated; and the other in which the raw materials stored in a raw material container is heat vaporized with a vaporizer. Any of the above types are applicable to the compounds of this invention. However, to produce thin films in a more stable manner, the system using a vaporizer is preferable. As to the heating temperature at the time of raw material vaporization, preferably it is 80 to 150° C. when heating the raw materials directly.

The methods for decomposing the raw material molecules having been vaporized and carried on the substrate surface are not limited to any specific ones, and any methods such as thermal CVD and plasma enhanced CVD can be employed. The thermal CVD is particularly preferable, because the system is simple and there is no concern about damage to the substrate since the decomposition temperature of the raw materials of this invention is relatively low. Preferably the ruthenium compounds are decomposed at substrate temperatures of 250° C. to 400° C.

In this CVD process, preferably a reduced pressure atmosphere is maintained inside the reactor. Reducing the pressure inside the reactor provides satisfactorily uniform film distribution and good step coverage. The preferable range of the pressure inside the reactor is 10 to 500 Pa.

DETAILED DESCRIPTION OF THE PREFERRED EMBODIMENTS

In the following this invention will be described in terms of its preferred embodiments.

First Embodiment

In this embodiment, bis(6-methyl-2,4-heptanedionate)(1,5-cyclooctadiene) ruthenium was prepared which had 1,5-cyclooctadiene, as a diene, and 6-methyl-2,4-heptanedione, as a β-diketone, coordinated with ruthenium.

Ruthenium trichloride hydrate ($RuCl_3 \cdot nH_2O$) was put in a 5 L separable flask so that the amount of ruthenium was 40.42 g, and 2700 mL of ethanol and 182 mL of 1,5-cyclooctadiene were added. This mixed solution was refluxed in the atmosphere for 8 hours, the resultant brown precipitate was filtrated, washed in ethanol and hexane, and vacuum dried. Thus, 103.6 g of (1,5-cyclooctadiene) ruthenium chloride as a precursor was obtained.

Then, 100 g of (1,5-cyclooctadiene)ruthenium chloride, 200 g of sodium carbonate anhydride, 2000 mL of dimethylformamide, and 150 g of 6-methyl-2,4-heptanedione were put in a 5 L separable flask, and the mixture was heated at 140° C. for one hour. After filtering this reaction solution, the filtrate was extracted with an ethyl acetate/10% aqueous solution of sodium hydroxide system, the ethyl acetate layer was concentrated and vacuum distilled, to prepare 121.6 g of bis(6-methyl-2,4-heptanedionate) (1,5-cyclooctadiene)ruthenium.

Second Embodiment

In this embodiment, bis(5-methyl-2,4-hexanedionate)(norbornadiene)ruthenium was prepared which had norbornadiene, as a diene, and 5-methyl-2,4-hexanedione, as a β-diketone, coordinated with ruthenium.

Ruthenium trichloride hydrate (40.42 g in terms of the amount of ruthenium), 2700 mL of ethanol and 165 mL of norbornadiene were put in a separable flask, and the mixed solution was refluxed in the atmosphere for 8 hours. The resultant brown precipitate was filtrated, washed in ethanol and hexane, and vacuum dried. Thus, 95.0 g of (norbornadiene)ruthenium chloride as a precursor was obtained.

Then, 100 g of (norbornadiene)ruthenium chloride, 200 g of sodium carbonate anhydride, 2000 mL of dimethylformamide, and 150 g of 5-methyl-2,4-hexanedione were put in a 5 L separable flask, and the mixture was heated at 140° C. for 3 hours. After filtering this reaction solution, the filtrate was extracted in the same manner as the first embodiment, the organic layer was concentrated and vacuum distilled, to prepare 130.2 g of bis(5-methyl-2,4-hexanedionate) (norbornadiene) ruthenium.

Third Embodiment

In this embodiment, bis(6-methyl-2,4-heptanedionate)(norbornadiene)ruthenium was prepared which had norbornadiene, as a diene, and 6-methyl-2,4-heptanedione, as a β-diketone, coordinated with ruthenium.

First, ruthenium trichloride hydrate and norbornadiene were reacted in ethanol in the same manner as the first embodiment to obtain 95.0 g of (norbornadiene)ruthenium chloride as a precursor.

Then, 100 g of (norbornadiene)ruthenium chloride, 200 g of sodium carbonate anhydride, 2000 mL of dimethylformamide, and 165 g of 6-methyl-2,4-heptanedione were put in a 5 L separable flask, and the mixture was heated at 140° C. for 3 hours. After filtering this reaction solution, the filtrate was extracted in the same manner as the first embodiment, the organic layer was concentrated and vacuum distilled, to prepare 133.6 g of bis(6-methyl-2,4-heptanedionate)(norbornadiene) ruthenium.

Fourth Embodiment

In this embodiment, bis(5-methyl-2,4-hexanedionate) (N,N,N',N'-tetramethylethylenediamine)ruthenium was prepared which had N,N,N',N'-tetramethylethylenediamine, as a diamine, and 5-methyl-2,4-hexanedione, as β-diketone, coordinated with ruthenium.

Ruthenium trichloride hydrate was put in a 5 L separable flask so that the amount of ruthenium was 80.15 g, and 3500 mL of water and 334.1 g of 5-methyl-2,4-hexanedione were added and the mixed solution was refluxed in the atmosphere for 2 hours. 330 g of sodium hydrogencarbonate was added to the solution, and the mixture was refluxed for another 2 hours. The resultant reaction solution was extracted with an ethyl acetate/10% aqueous solution of sodium hydroxide system, the ethyl acetate layer was evaporated to dryness, to obtain 285.3 g of red crystal of tris(5-methyl-2,4-hexanedionate) ruthenium.

Then 100 g of tris(5-methyl-2,4-hexanedionate) ruthenium, 240 g of N,N,N',N'-tetramethylethylenediamine, 250 g of zinc, 3000 mL of ethanol, and 500 mL of water were put in a 5 L separable flask, and the mixture was refluxed in the nitrogen atmosphere for 24 hours. After filtered/concentrated, the resultant reaction solution was extracted with an ethyl acetate/10% aqueous solution of sodium hydroxide system, and the ethyl acetate layer was concentrated, purified by gas chromatography, and vacuum distilled, to prepare 89.6 g of bis(5-methyl-2,4-hexanedionate) (N,N,N',N'-tetramethylethylenediamine) ruthenium.

Fifth Embodiment

In this embodiment, bis(2,4-hexanedionate)di(acrylonitrile)ruthenium was prepared which had acrylonitrile, as two organic ligands, and 2,4-hexanedionate, as β-diketone, coordinated with ruthenium.

Ruthenium trichloride hydrate was put in a 5 L separable flask so that the amount of ruthenium was 80.15 g, and 3500 mL of water and 297.5 g of 2,4-hexanedione were added and the mixed solution was refluxed in the atmosphere for 2 hours. Then 330 g of sodium hydrogencarbonate was added to the solution, and the mixture was refluxed for another 2 hours. The resultant reaction solution was extracted, the organic layer was evaporated to dryness, to obtain 285.3 g of red crystal of tris(2,4-hexanedionate) ruthenium.

Then 100 g of tris(2,4-hexanedionate)ruthenium, 220 g of acrylonitrile, 250 g of zinc, 3000 mL of ethanol, and 500 mL of water were put in a 5 L separable flask, and the mixture was refluxed in the nitrogen atmosphere for 24 hours. This reaction solution was filtered/concentrated, extracted, purified by gas chromatography and vacuum distilled in the same manner as the fourth embodiment, to prepare 90.7 g of bis(2,4-hexanedionate)di(acrylonitrile)ruthenium.

Then, of the organic ruthenium compounds thus prepared, the compounds of the second and third embodiments were subjected to thermogravimetric—differential thermal analysis (TG-DTA). The measurement was made at heating rate of 5° C./min in the flowing argon. For comparison, TG-DTA analysis was also conducted for tris(2,4-octanedionate) ruthenium.

As a result, the 50% weight loss temperatures of the organic ruthenium compounds of the second and third embodiments were 234° C. (percentage loss of weight 99%) and 246° C. (percentage loss of weight 97%), respectively, in contrast with 273° C. (percentage loss of weight 99%) for tris(2,4-octanedionate)ruthenium. This shows that in the organic ruthenium compounds of the second and third embodiments, their vaporization temperatures are low and their percentage losses of weight are high, therefore, efficient vaporization (thin film production) is possible.

Then, ruthenium thin films were produced from the organic ruthenium compounds of the first to sixth embodiments, as raw materials, by CVD. In the CVD, thin films were produced with a system in which the raw material compounds were dissolved in methanol as a solvent, the solutions were vaporized with a vaporizer, and the raw material gases are fed on the surfaces of the respective substrates.

Concentration of Solution: 0.5 mol/L
Solution Feed Rate: 0.05 mL/min
Vaporization Temperature: 190° C.
Carrier Gas: argon (500 sccm)
Reaction Gas: oxygen (25 sccm)
Chamber Pressure: 133 Pa (1 torr)
Substrate: $SiO_2$ wafer
Substrate Temperature: 310° C.
Film Formation Time: 20 minutes As a comparative example, a ruthenium thin film was produced from bis(ethylcyclopentadienyl)ruthenium as a raw material. In this comparative example, the thin film was produced with a system in which the stock solution of the raw material compound (concentration 100%) was heated by a vaporizer. The production conditions were as follows.

Raw Material Feed Rate: 0.005 g/min
Vaporization Temperature: 190° C.
Carrier Gas: argon (200 sccm)
Reaction Gas: oxygen (200 sccm)
Chamber Pressure: 666 Pa (5 torr)
Substrate: $SiO_2$ wafer
Substrate Temperature: 250° C.
Film Formation Time: 20 minutes In the above thin film production, ruthenium thin films were produced without any trouble. Then a test was conducted to examine the adhesion properties of the thin films (hereinafter referred to as peel test). The peel test was conducted in such a manner as to form grids 5 mm×5 mm (1600 grids in total) in the area of 20 cm×20 cm on a wafer on which a thin film has been formed, stick a commercially available cellophane tape on and peel the same from the grids, and determine the number of grids under which the ruthenium thin film has been peeled from the wafer. The results are shown in Table 1.

Table 1

TABLE 1

|  | Number of Grids under Which Thin Film has been peeled |
|---|---|
| First Embodiment | 0 |
| Second Embodiment | 0 |
| Third Embodiment | 2 |
| Fourth Embodiment | 0 |
| Fifth Embodiment | 1 |
| Comparative Example | 35 |

It was confirmed, from the results of the peel test, that the thin films produced using the organic ruthenium compounds having been produced in the embodiments of this invention all had good adhesion to the substrate.

It was also confirmed, from the results of the TG-DTA analysis together with those of the peel test, that the organic ruthenium compounds embodying this invention excelled in handling properties, in terms of physical properties such as vapor pressure, enabled the production of thin films of good quality, that is, thin films of good adhesion and were very preferable as CVD raw materials.

What is claimed is:

1. Raw material compounds for use in CVD which contain organic ruthenium compounds as a main ingredient, wherein the organic ruthenium compounds have two β-diketones and one diene coordinated with ruthenium as shown by the following structural formula:

[Chemical Formula 1]

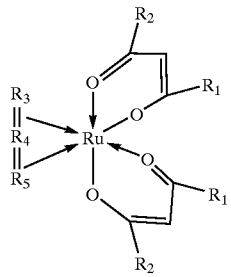

wherein the substituents $R_1$, $R_2$ of the β-diketones are alkyl groups, the total number of carbon atoms contained in $R_1$, $R_2$ is 3 to 5, and the organic groups $R_3$, $R_4$, $R_5$ constituting the diene may be linked to one another to form a ring.

2. The raw material compounds for use in CVD according to claim 1, wherein the diene coordinated with ruthenium is selected from the group consisting of 1,4-cyclohexadinene, norbornadiene and 1,5-cyclooctadinene.

3. Raw material compounds for use in CVD which contain organic ruthenium compounds as a main ingredient, wherein the organic ruthenium compounds have two β-diketones and one diamine coordinated with ruthenium as shown by the following structural formula:

[Chemical Formula 2]

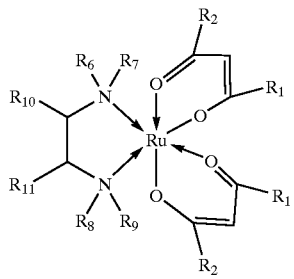

wherein the substituents $R_1$, $R_2$ of the β-diketones are alkyl groups, the total number of carbon atoms contained in $R_1$, $R_2$ is 2 to 5, the substituents $R_6$, $R_7$, $R_8$, $R_9$, $R_{10}$ and $R_{11}$ of the diamine are independently selected from the group consisting of hydrogen and alkyl group, and the total number of carbon atoms contained in $R_6$, $R_7$, $R_8$, $R_9$, $R_{10}$ and $R_{11}$ is 2 to 8.

4. The raw material compounds for use in CVD according to claim 3, wherein the diamine coordinated with ruthenium is N,N,N',N'-tetramethylethylenediamine.

5. Raw material compounds for use in CVD which contain organic ruthenium compounds as a main ingredient, wherein the organic ruthenium compounds have two β-diketones and two organic ligands coordinated with ruthenium as shown by the following structural formula:

[Chemical Formula 3]

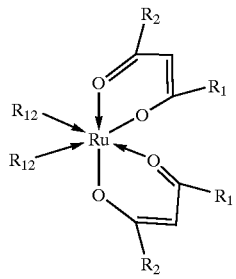

wherein the substituents $R_1$, $R_2$ of the β-diketones are alkyl groups, the total number of carbon atoms contained in $R_1$, $R_2$ of the β-diketone ring is 2 to 5, and each organic ligand $R_{12}$ is independently selected from the group consisting of olefin, amine, and carbonyl.

6. The raw material compounds for use in CVD according to claim 5, wherein $R_{12}$ is an olefin, wherein said olefin is selected from the group consisting of ethylene, propylene, 2-methylpropylene, butene and 1,3-butadiene.

7. The raw material compounds for use in CVD according to claim 5, wherein $R_{12}$ is an amine, wherein said amine is selected from the group consisting of trimethylamine and triethylamine.

8. The raw material compounds for use in CVD according to claim 1, wherein the β-diketone has an asymmetrical shape where $R_1$ and $R_2$ are different substituents.

9. The raw material compounds for use in CVD according to claim 4, wherein the two β-diketones coordinated with ruthenium are selected from the group consisting of 2,4-hexanedione, 5-methyl-2,4-hexanedione, 2,4-heptanedione, 5-methyl-2,4-heptanedione, 6-methyl-2,4-heptanedione and 2,4-octanedione.

10. A method for producing ruthenium or ruthenium compound thin films on a substrate by chemical vapor deposition, comprising the steps of: vaporizing the raw material compounds for CVD according to claim 1; carrying the vaporized raw material compounds on the substrate; and decomposing the raw material compounds to deposit ruthenium or the ruthenium compounds on the substrate.

* * * * *